United States Patent [19]

Schulz, Jr. et al.

[11] Patent Number: 5,196,559
[45] Date of Patent: Mar. 23, 1993

[54] EQUILIBRATION OF CYCLIC SILOXANES WITH NOVEL CATALYSTS

[75] Inventors: William J. Schulz, Jr., Midland, Mich.; Joseph B. Lambert, Glenview, Ill.; Lidia Kania, Warsaw,

[73] Assignee: Dow Corning Corporation, Midland, Mich.

[21] Appl. No.: 824,664

[22] Filed: Jan. 23, 1992

[51] Int. Cl.$^5$ .............................................. C07F 7/08
[52] U.S. Cl. .................................... 556/460; 556/461; 556/462
[58] Field of Search ..................... 556/462, 460, 461

[56] References Cited

U.S. PATENT DOCUMENTS

| | | |
|---|---|---|
| 3,642,851 | 2/1972 | Bennett ........................... 556/460 X |
| 3,646,088 | 2/1972 | Bakarsian et al. ............... 556/460 X |
| 4,008,261 | 2/1977 | Brown et al. ....................... 556/462 |
| 4,222,952 | 9/1980 | Vich ..................................... 556/462 |
| 4,348,531 | 9/1982 | Evans ............................... 556/462 X |
| 4,719,276 | 1/1988 | Stebleton ......................... 556/462 X |
| 4,888,405 | 12/1989 | Ganiou et al. .................. 556/462 X |
| 4,895,968 | 1/1990 | Buese et al. ......................... 556/462 |
| 4,948,907 | 8/1990 | Fleischmann et al. ............. 556/462 |
| 5,068,383 | 11/1991 | Bourgoin ........................ 556/460 X |
| 5,087,683 | 2/1992 | Arai et al. ....................... 556/462 X |

*Primary Examiner*—Paul F. Shaver
*Attorney, Agent, or Firm*—Robert L. McKellar

[57] ABSTRACT

A process for preparing cyclosiloxanes by the redistribution of a cyclosiloxane or mixture of cyclosiloxanes in the presence of a rearrangement catalyst.

17 Claims, No Drawings

EQUILIBRATION OF CYCLIC SILOXANES WITH NOVEL CATALYSTS

BACKGROUND OF THE INVENTION

This invention relates to a process for preparing cyclosiloxanes, more particularly a process for reacting cyclosiloxanes with a rearrangement catalyst to yield higher molecular weight oligomers.

In a publication authored by Chojnowski, J.; Mazurek, M.; Scibiorek, M.; Wilczek, L., "Cationic Polymerization of Siloxanes" Die Macromolekulare Chemie 175, pp. 3299–3303, 1974, there is described the polymerization of hexamethylcyclotrisiloxane and octamethylcyclotetrasiloxane in the presence of protonic or Lewis acids. It is theorized by these authors that higher molecular weight polymers are formed by attaching cyclic monomers to the end of a growing macromolecular chain, which according to these authors, is consistent with the conventional understanding of cationic ring-opening polymerization reactions. They indicated that the structure of the active center of propagation and the way it reacts with the monomer is not clear, but oxonium ion, silicenium (silylenium) ion and free radical structures are postulated. The catalysts used in these polymerization reactions were $CF_3SO_3H$ for both hexamethylcyclotrisiloxane and octamethylcyclotetrasiloxane and $C_3H_5O_2SbF_6$ for octamethylcyclotetrasiloxane. Negligible amounts of higher oligomers were detected in this work.

In addition to the polymerization of cyclosiloxanes with catalysts, it has been known for some time that cyclosiloxanes containing more than four silicon atoms are produced in minute quantities during the commercial preparation of cyclosiloxane oligomers. These higher molecular weight cyclosiloxane oligomers having more than four silicon atoms can be isolated from lower molecular weight polymer mixtures having three or four silicon atoms only through laborious separation techniques; consequently if the yield of higher molecular weight polymers were increased the result would be an increase in yield efficiency after separation from the lower molecular weight polymers. Thus, it is beneficial to the art to have available a more efficient and economical process for producing higher quantities of cyclosiloxanes having more than four silicon atoms.

An advantage of the instant invention is the utilization of specific rearrangement catalysts to improve the efficiency of the reactions currently employed to produce higher molecular weight cyclic siloxanes.

Another advantage of the invention is the capability to selectively increase the yield of a specific molecular weight cyclosiloxane.

SUMMARY OF THE INVENTION

The present invention relates to a process for preparing cyclosiloxanes comprising contacting at least one cyclic siloxane with at least one catalyzing organosilicon compound at a temperature and a time sufficient to redistribute the cyclosiloxanes under anhydrous conditions.

Cyclosiloxanes useful in this invention have the general formula $(R_2SiO)x$ wherein each R is independently selected from hydrogen, alkyl, alkenyl, aryl, aralkyl, haloalkyl, alkylthio, arylthio, alkoxy, diakylamino, diarylamino, alkylarylamino, aryloxy, and alkaryl groups having one to sixteen carbon atoms; and x is an integer having a value of from three to twelve.

Materials representing the catalyzing organosilicon compound have the following structures:

wherein R" and R' are defined the same as R with the exception R' cannot be hydrogen. In this formula, "A" is a non-nucleophilic anion, that may be represented by structures such as $OSO_2CF_3$, $BPh_4$, I, Br, and $ClO_4$. n is an integer having a value of from two to seven.

The primary objective of this invention is to provide an improved process over those currently employed for preparing higher molecular weight cyclosiloxanes. These and other features and advantages of the invention herein described will become more readily apparent when considered in light of the detailed description that follows.

DETAILED DESCRIPTION OF THE INVENTION

The present invention relates to a process for preparing cyclosiloxanes comprising contacting at least one cyclic siloxane (1) with at least one catalyzing organosilicon compound (2) at a temperature and a time sufficient to redistribute the cyclosiloxane (1) under anhydrous conditions.

In using the term "contacting", it is meant that the compounds (1) and (2) may be physically combined in any order and manner without detracting from the reaction. For example, one may add the cyclosiloxane or cyclosiloxane mixture (1) to the catalyzing organosilicon compound (2), or one may add the catalyzing organosilicon compound to the cyclosiloxane, either in the presence or absence of a solvent. Solvents are not essential to practice the invention, but one may add the individual compounds (1) and (2) separately to a suitable solvent (3). Examples of solvents useful in the invention include $CH_2Cl_2$, $CH_3CN$, $CH_3CCl_3$, $CCl_4$, $CHCl_3$, sulfolane, $ClCH_2CH_2Cl$, benzene, toluene, THF, and diethyl ether, wherein $CH_3CN$, benzene, toluene and $CH_2Cl_2$ are preferred.

The cyclosiloxanes useful in the redistribution process of this invention have the general formula $(R_2SiO)x$ wherein R is independently selected from hydrogen, alkyl, diakylamino, diarylamino, alkylarylamino aryl, alkenyl, aralkyl, haloalkyl, thioalkyl, thioaryl, alkoxy, aryloxy, and, alkaryl, groups having one to sixteen carbon atoms; and x is an integer having a value of from three to twelve. Further, it should be understood that the R radicals on the silicon atoms can be the same or different. Illustrative examples of the above groups include alkyls such as methyl, ethyl, propyl, isopropyl, butyl, isobutyl, tert-butyl, and the like; aryl groups such as phenyl, naphthyl, and the like; aralkyl groups such as benzyl, phenylethyl tolyl, anisolyl, and the like; alkenyl groups such as vinyl, allyl, 5-hexenyl, and the like; haloalkyl groups such as 2-chloroethyl, 3-bromohexyl, iodomethyl, and the like; alkylthio groups such as methylthio, (2-propyl)thio, ethylthio, and the like; dialkylamino groups such as dimethylamino, diisopropylamino, ethylmethylamino, and the like; diarylamino groups such as diphenylamino, phenyl-p-tolylamino, (o-chlorophenol)-p-butylphenylamino and the like; alkylarylamino groups such as methylphenylamino, propyl-p-tolylamino, isopropyl-(o-chlorophenol)amino and the like; arylthio groups such as phenylthio, p-tolylthio, napthylthio, and the like; alkoxy groups such as methoxy, isopropoxy, t-butoxy and the like; aryloxy groups such as phenoxy, p-methylphenoxy, m-butylphenoxy, and the like; alkaryl groups such as p-tolyl, o-ethylphenyl, m-butylphenyl, and the like. Among the preferred cyclosiloxanes are hexamethylcyclotrisiloxane, tetramethylcyclotetrasiloxane, octamethylcyclotetrasiloxane, wherein hexamethylcyclotrisiloxane and octamethylcyclotetrasiloxane are more preferred, and furthermore hexamethylcyclotrisiloxane is most preferred.

The catalyzing organosilicon compounds useful in the present invention are of the foregoing type, and can be more particularly illustrated by the formulas (R'$_3$SiA) and

wherein R' and R" are defined as above R with the exception R' cannot be hydrogen. R' and R" are independently selected from alkyl, aryl, aralkyl, haloalkyl, alkylthio, arylthio, alkoxy, alkenyl, diakylamino, diarylamino, alkylarylamino, aryloxy, and alkaryl groups having one to sixteen carbon atoms. n is an integer having a value of from two to seven. In the general formula "A" is defined as an anion, wherein A includes structures such as $OSO_2CF_3$, $Bph_4$, I, Br, and $ClO_4$. The most preferred anions are $ClO_4$ and $OSO_2CF_3$. Materials such as those containing —SH, —OH, COOH, NH, $NH_2$, $SO_3$—H and the like are not useful in this invention. Preferably in the use of the invention, the concentration of the catalyzing organosilicon compound is between $10^{-6}$ to $10^{-2}$ moles per liter of solution.

In accordance with the preferred use of the invention, the process conditions are reaction temperatures between $-78°$ C. to $80°$ C., preferably between $25°$ C. to $80°$ C., although the most preferred temperature is between $25°$ C. to $50°$ C. The process pressure is not critical; therefore the reaction can be run at sub-atmospheric, atmospheric, or super-atmospheric pressures; however atmospheric pressure or above are preferred. The time for the reaction to take place is generally between 1 to 72 hours, but the time for the reaction is highly dependent on the time taken for the system to reach equilibrium. Further, it should be understood that the desired product can be obtained by stopping the equilibration at exactly the desired time. Commonly between 2 to 50 hrs. are used; however, reaction times between 2 to 30 hrs. are preferable.

It is believed that in this invention there is an interaction of the cyclosiloxane with the catalyzing organosilicon compound whereby a bond contained in the cyclosiloxane molecular ring is cleaved, consequently opening the ring and exposing a reactive end of the molecule. The active end then becomes the catalyzing species and attacks another cyclosiloxane molecule to propagate the oligomerization. Ring closure occurs by backbiting of the one reactive end on the siloxane chain.

In the case of the preferred use of the process according to the invention, the reaction is performed ideally under anhydrous conditions, with the further proviso that there cannot be present any compound having an active hydrogen atom. Water should be avoided or the predominant reaction will be the hydrolysis of the catalyst; thus exposure to atmospheric moisture should be avoided by providing an inert dry gaseous blanket. Dry nitrogen, helium, argon, and the like are suitable blanket gases with argon most preferred. Precaution should be used when common nitrogen gases are used as a blanket, as nitrogen may not be dry enough because it is susceptible to moisture entrainment and could require an additional drying step before use herein. Ideally there should be at least one molecule more catalyst than active hydrogen in the system, but it is preferred that the minimum catalyst concentration be $10^{-6}$ moles per liter of solution.

The following example is illustrative of a method for the preparation of the compound $(Me_2SiO)_5$, wherein Me is methyl. The invention is believed to proceed by the following set of reactions, but the invention herein should not be held to such a theory.

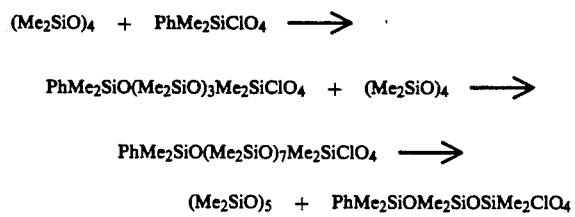

EXAMPLE I

To 30 ml of 0.95M hexamethylcyclotrisiloxane ($D_3$) in freshly purified and dried $CH_2Cl_2$, 1 ml of phenyldimethylsilyl perchlorate catalyst solution (in either $CH_2Cl_2$ or $CH_3CN$) was syringed into a flask under a dry nitrogen blanket to yield a catalyst concentration of $5.9 \times 10^{-4}$M. The mixture remaining under the dry nitrogen blanket was stirred for 2 hours at $24°$ C., and quenched with 0.5 ml of deionized water. The reaction mixture was washed with deionized water and the organic portion was dried overnight with $CaH_2$. After filtration to remove the drying agent and rotary evaporation to remove the solvent, the resulting thick, colorless oil was subjected to analysis by gas chromatography and mass spectrometry. The resulting products are presented in TABLE I (values are area % by GLC).

TABLE I

| Product yields from the reaction of 0.95M $D_3$ with 0.006M $PhMe_2SiClO_4$ in $CH_2Cl_2$ or $CH_3CN$. | | |
|---|---|---|
| Product | $CH_2Cl_2$ Solvent (Area %) | $CH_3CN$ Solvent (Area %) |
| $D_3$ | <1 | 56 |
| $D_4$ | 34 | 13 |
| $D_5$ | 37 | 1 |
| $D_6$ | 14 | 10 |
| $D_7$ | 3 | — |
| $D_8$ | 1 | — |
| $D_9$ | 1 | 6 |
| $D_{10}$ | 1 | — |
| $D_{11}$ | 1 | — |
| $D_{12}$ | 1 | — |

NOTE: "—" indicates none detected.

EXAMPLE II

To 30 ml of 0.95M octamethylcyclotetrasiloxane ($D_4$) in freshly purified and dried $CH_2Cl_2$, 1 ml of phenyldimethylsilyl perchlorate catalyst solution (in either $CH_2Cl_2$ or $CH_3CN$) was syringed into a flask under a dry nitrogen blanket to yield a catalyst concentration of $5.9 \times 10^{-4}$M. The reaction mixture was stirred for 2 hours and then worked up in the same manner as Example I, with the exception that no solvents were present in some runs. In the case of the neat reactions, the catalyst was generated in the indicated solvent prior to introduction into the reaction medium. The resulting products are presented in TABLE II.

TABLE II

Product yields from the reaction of 0.95M $D_4$ with 0.006M $PhMe_2SiClO_4$, neat or in $CH_2Cl_2$ or $CH_3CN$.

| Product | Neat (GLC Area %; Catalyst formed in $CH_2Cl_2$) | Neat (GLC Area %; Catalyst formed in $CH_3CN$) | $CH_2Cl_2$ Solvent (GLC Area %) | $CH_3CN$ Solvent (GLC Area %) |
|---|---|---|---|---|
| $D_4$ | 99 | 99 | 83 | 99 |
| $D_5$ | <1 | 1 | 9 | <1 |
| $D_6$ | <1 | <1 | 12 | <1 |
| $D_7$ | <1 | <1 | 2 | <1 |
| $D_8$ | <1 | <1 | <1 | — |
| $D_9$ | <1 | <1 | <1 | — |

NOTE: "—" indicates none detected.
The catalyst in $CH_2Cl_2$ solvent gave the best results as indicated by TABLE II.

EXAMPLE III

To 14 ml (1.6 grams) of hexamethylcyclotrisiloxane ($D_3$) and 2.12 grams of octamethylcyclotetrasiloxane ($D_4$) in purified and dried $CH_2Cl_2$, 1 ml of phenyldimethylsilyl perchlorate in $CH_2Cl_2$ was injected under a dry nitrogen blanket using a syringe to produce a catalyst concentration of $6.0 \times 10^{-4}$M. The mixture was stirred for 2 hours at 24° C. and quenched with 0.5 ml of deionized water. The reaction mixture was dried over $CaH_2$ overnight, filtered, and subjected to rotary evaporation for solvent removal. The residue was analyzed by gas chromatography. The resulting products are presented in TABLE III.

TABLE III

Product yields from the reaction of 0.95M $D_3$ and $D_4$ with 0.006M $PhMe_2SiClO_4$ in $CH_2Cl_2$ or $CH_3CN$.

| Product | $CH_2Cl_2$ Solvent (GLC Area %) | $CH_3CN$ Solvent (GLC Area %) |
|---|---|---|
| $D_3$ | <1 | 9 |
| $D_4$ | 63 | 69 |
| $D_5$ | 20 | 1 |
| $D_6$ | 10 | 10 |
| $D_7$ | 3 | — |
| $D_8$ | 1 | 4 |
| $D_9$ | 1 | — |

NOTE: "—" indicates none detected.

EXAMPLE IV

To 2.405 grams of tetramethylcyclotetrasiloxane ($D'_4$) in a flask under dry nitrogen, was added 2 milligrams of phenylidimethylsilyl perchlorate to yield an effective catalyst concentration of $5.9 \times 10^{-4}$M. The reaction mixture was stirred for 2 hours or 20 hours and then worked up in the same manner as Example I, with the exception that no solvents were present in some runs. In the case of the neat reactions, the catalyst was generated in the indicated solvent prior to introduction into the reaction medium. The resulting products are presented in TABLE IV.

TABLE IV

Product yields from the reaction of 0.95M $D'_4$ with 0.006M $PhMe_2SiClO_4$, neat or in $CH_2Cl_2$ or $CH_3CN$.

| Product | Neat (GLC Area %; Catalyst formed in $CH_2Cl_2$) | Neat (GLC Area %; Catalyst formed in $CH_3CN$) | $CH_2Cl_2$ (GLC Area %) | $CH_3CN$ (GLC Area %) |
|---|---|---|---|---|
| | 2 h/20 h | 2 h/20 h | 2 h/20 h | 2 h/20 h |
| $D'_4$ | 97/— | 96/a | 96/97 | 82/37 |
| $D'_5$ | 1/— | 1/a | 1/1 | 5/27 |
| $D'_6$ | —/— | <1/a | —/— | —/— |
| $D'_7$ | —/— | —/a | —/— | —/— |
| $D'_8$ | —/— | —/a | —/— | 1/4 |

NOTE:
"a" indicates experiment not performed.
"—" indicates none detected.

EXAMPLE V

To 2.405 grams of tetramethylcyclotrasiloxane ($D'_4$) in a flask under dry nitrogen, was added 2 milligrams of triphenylmethyl perchlorate ($Ph_3CClO_4$) yielding an effective catalyst concentration of $5.9 \times 10^{-4}$M. The reaction mixture was stirred for 2 hours or 20 hours then worked up in the same manner as Example I. The resulting products are presented in TABLE V.

TABLE V

Product yields from the reaction of 0.95M $D'_4$ with 0.006M $Ph_3CClO_4$ in $CH_2Cl_2$ or $CH_3CN$.

| Product | $CH_2Cl_2$ Solvent (GLC Area %) | $CH_3CN$ Solvent (GLC Area %) |
|---|---|---|
| | 2 h/20 h | 2 h/20 h |
| $D'_4$ | —/96 | 71/35 |
| $D'_5$ | —/1 | 9/21 |
| $D'_6$ | —/<1 | 3/8 |
| $D'_7$ | —/— | —/— |

NOTE: "—" indicates none detected.

Numerous modifications and variations of this invention will be obvious to a worker skilled in the art and it is understood that such modifications and variations are to be included within scope of this application and the appended claims.

That which is claimed is:

1. A process, said process comprising, contacting at least one cyclic siloxane with at least one catalyzing organosilicon compound at a temperature and a time sufficient to redistribute said cyclic siloxane under anhydrous conditions.

2. A process, said process comprising, contacting at least one cyclic siloxane having the general formula $(R_2SiO)x$ with a catalyzing organosilicon compound having the general formulas $(R'_3SiA)$ and

at a temperature from −78° C. to 80° C.; and for a time of 1 to 72 hours under anhydrous conditions wherein R' and R" are selected from the group comprising alkyl, aryl, aralkyl, alkenyl, haloalkyl, thioalkyl, diakylamino, diarylamino, alkylarylamino, thioaryl, alkoxy, aryloxy, and alkaryl groups having one to sixteen carbon atoms; and R and R" are hydrogen or R'; x is an integer having a value of from three to twelve; n is an integer having a value of from two to seven; and A is a non-nucleophilic anion.

3. The process of claim 2, wherein each alkyl group is methyl.

4. The process of claim 2, wherein R is methyl and R' is phenyl.

5. The process of claim 2, wherein the temperature range is 25° C. to 80° C.

6. The process of claim 2, wherein the temperature is from 25° C. to 50° C.

7. The process of claim 2, wherein the time is from 2 to 50 hours.

8. The process of claim 2, wherein the time is from 2 to 30 hours.

9. The process of claim 2, wherein additionally a solvent is present.

10. The process of claim 9, wherein said solvent is $CH_2Cl_2$.

11. The process of claim 9, wherein said solvent is $CH_3CN$.

12. The process of claim 2, wherein the siloxanes $(R_2SiO)x$ are a mixture of cyclic siloxanes.

13. The process of claim 2, wherein the concentration of $R'_3SiA$ is $10^{-5}$ to $10^{-2}$ moles per liter.

14. The process of claim 2, wherein the contact takes place using an inert gas atmosphere.

15. The process of claim 14, wherein the said gas is selected from a group consisting essentially of argon, nitrogen and helium.

16. The process of claim 2, wherein $R'_3SiA$ is $PhMe_2SiClO_4$.

17. The process of claim 2, wherein

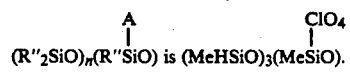

$(R''_2SiO)_n(R''SiO)$ is $(MeHSiO)_3(MeSiO)$.

* * * * *